United States Patent [19]

Hurley et al.

[11] Patent Number: 5,256,571
[45] Date of Patent: Oct. 26, 1993

[54] CELL PRESERVATIVE SOLUTION

[75] Inventors: Anne A. Hurley, Carver; Daniel C. Lapen, Lancaster, both of Mass.; Peter S. Oud, Bennebroek, Netherlands

[73] Assignee: Cytyc Corporation, Marlboro, Mass.

[21] Appl. No.: 694,452

[22] Filed: May 1, 1991

[51] Int. Cl.$^5$ .................... G01N 31/00; A01N 1/02
[52] U.S. Cl. ........................... 436/17; 436/18; 436/8; 436/826; 435/1; 435/2
[58] Field of Search ............... 435/1, 2, 240.1, 240.2, 435/800; 436/17, 18, 826, 8

[56] References Cited

U.S. PATENT DOCUMENTS

| | | | |
|---|---|---|---|
| 4,090,977 | 5/1978 | Dubin | 436/18 |
| 4,390,632 | 6/1983 | Carter, II | 435/183 |
| 4,493,821 | 1/1985 | Harrison | 436/18 |

FOREIGN PATENT DOCUMENTS

| | | |
|---|---|---|
| 0049478 | 4/1982 | European Pat. Off. |
| 0431385 | 6/1991 | European Pat. Off. |
| 2099281 | 12/1982 | United Kingdom |

OTHER PUBLICATIONS

WPI, File Supplier, Accession No. 74-81767V (47), Derwent Publications Ltd. London, GB; & JP-A-49 039 437 (Toa Tokushu Denki Co., Ltd) Oct. 25, 1974.
Maitland et al., "Freeze-substitution Staining of Rat Growth Plate Cartilage With Alcian Blue for Electron Microscopic Study of Proteoglycans[1]", *The Journal of Histochemistry and Cytochemistry*, vol. 37, No. 3, pp. 383-387, 1989.
Kurki et al., "Monoclonal antibodies to proliferating cell nuclear antigen (PCNA)/cyclin as probes for proliferating cells by immunofluorescence microscopy and flow cytometry", *Jour. of Immunological Methods*, 109 (1988) pp. 49-59.
Campana et al.,. "Double and triple staining methods for studying the proliferative activity of human B an T lymphoid cells", *Journal of Immunological Methods*, 107 (1988) pp. 79-88.
Ronne, "Chromosome Preparation and High Resolution Banding Techniques. A Review.", Symposium: Cytogenetics and Cell Biology, *J. Dairy Sci.*, 72:1363-1377, (1989).
Levitt et al., "Methanol fixation permits flow cytometric analysis of immunofluorescent stained intracellular antigens", *Journal of Immunological Methods*, 96 (1987) 233-237.
Gill et al., "Laboratory Cytopathology Techniques For Specimen Preparation", The Johns Hopkins Hospital, Sixth Edition, 1980, pp. 3-1-3-3.
Pearson et al., "Evaluation of Collection and Preservation Techniques for Urinary Cytology", Acta Cytologica, 25(3): (May-Jun. 1981), pp. 327-333.
Tsuchihashi et al., "Quantification of Nuclear DNA and Intracellular Glycogen in a Single Cell by Fluorescent Double-Staining", Histochemistry, 63. 311-322 (1979).
Koss, *Diagnostic Cytology and Its Histopathologic Bases*, vol. Two, pp. 1187-1202.
Keebler et al., *A Manual of Cytotechnology*, Sixth Edition, American Society of Clinical Pathologists Press, 1983, pp. 321-322.
Villanueva, A. R., J. Histotechnology, 9(3). 1986. pp. 155-161 (Biosis Abstract).
Rost et al, Histochem. J., 7(4), Jul. 1975, pp. 307-320 (Biosis Abstract).
Baumgaertner et al, J. Clin. Microbiol., 26(10) 1988 pp. 2044-2047 (Biosis Abstract).
Kehr et al, Biologia, 39(11), 1984) p. 1107-1114 (Biosis Abstract).

*Primary Examiner*—Douglas W. Robinson
*Assistant Examiner*—Susan M. Weber
*Attorney, Agent, or Firm*—Lahive & Cockfield

[57] ABSTRACT

An aqueous alcohol buffer solution for substantially ambient, in vitro preservation of mammalian cells for a selected duration. The solution generally contains a water-miscible alcohol in an amount sufficient to fix the sample cells without coagulation, an anti-clumping agent, and a buffer agent to maintain the solution at a pH within a range of four to seven.

15 Claims, No Drawings

CELL PRESERVATIVE SOLUTION

BACKGROUND

This invention relates to a solution and method for preservation of cells at ambient temperatures. The solution and method provide rapid fixation of live cells for subsequent analysis.

It is known in the clinical and research arenas that preservation of cell samples for subsequent analysis is desirable. From a diagnostic standpoint, a specimen is most valuable when it is fresh. The more time that elapses between collection of a specimen and its fixation on a slide or other matrix, the less integrity is retained. Depriving cells of the physiologic conditions of its donor for long periods of time, i.e., minutes, allows autolysis to begin.

In a clinical setting it is often necessary to take samples, e.g., vaginal cells or muscle cells from a patient, which are later stained for histology analysis. Such histochemical staining has unquestionable value in the interpretation and study of cell physiology and pathology, however the staining cannot usually be performed simultaneous with the sampling. It is often desirable to perform a biopsy on a patient at one time, and to perform cytological or histological analysis of the collected cells or tissue at a different time. Calls often lose integrity in that interim period, thus diminishing the value of the subsequent analysis.

Several types of saline, or balanced salt, solutions are commercially available for preserving cell specimens in the interim between sampling and fixation and/or analysis. A few of these solutions includes Hanks' balanced salt solution, a minimal essential (MEM) tissue culture medium, Polysal ®, and normal saline. The high cost of some medium, such as Hanks' and MEM, prohibits its routine use.

Polysal ®, available from Cutter Biologicals, Emeryville, Calif., is a balanced polyionic electrolyte solution containing sodium chloride, calcium, and magnesium at a physiologically equivalent concentration to normal human plasma. Although an adequate saline solution for relatively short-term storage, it neither inhibits bacterial growth nor enables extended ambient storage.

Hanks' BSS is a modified Ringer solution. It is designed to maintain osmotic pressure within physiologic limits, maintain optimal pH range by including buffer systems, and provides an adequate concentration of inorganic ions for normal cell metabolism. This solution includes a glucose energy source. However, cells lose viability after an exposure of over twenty minutes, which affects cytopathologic analysis.

Many types of clinical tissue and cell samples contain extraneous proteins which interfere with subsequent staining and analysis. Placement of specimen cells in a saline solution does not address some auxiliary problems with such sample integrity. Extended preservation of specimens often results in bacteria growth, which is also nurtured by the balance of prior art normal or augmented saline solutions.

Accordingly, it is an object of the present invention to provide a cell fixing solution and process which preserves cells and tissue for subsequent cytological or histological analysis.

SUMMARY

This invention generally relates to a solution and method for preservation of cells and tissue at ambient temperatures. The solution is an alcohol buffer solution for in vitro preservation of mammalian cells at ambient temperatures following biopsy, and prior to staining or other forms of analysis. In one embodiment, the preservation solution provides a medium for relatively long-term ambient preservation. In another embodiment, the preservation solution provides a medium for transportation and removal of undesired protein from the sample solution.

More specifically, a preservative solution according to the invention has water-miscible alcohol, in combination with an anti-clumping agent and a buffering agent. The alcohol constituent is present in an amount sufficient to fix sample cells or tissue, while the anti-clumping agent is present in an amount sufficient to prevent cells from clumping in solution. The buffering agent is one which maintains the pH of the solution within a range of between about four to about seven for the duration of preservation.

In a preferred embodiment of the invention, the alcohol is one from the group consisting of ethanol and methanol. The anti-clumping agent is a chelating agent, preferably one from the group consisting of ethylenediaminetetra-acetic acid (EDTA), and its salts, such as disodium, tripotassium and tetrasodium. The buffering agent is selected from PBS, Tris buffer sodium acetate, and citric acid. EDTA and its malts may also be used as a buffering agent. In one preferred embodiment, the solution comprises methanol, EDTA, and sodium acetate. In that embodiment, the solution constitutes about 45–55 percent methanol, the EDTA, in the form of glacial acetic acid, constitutes about 2–4 percent, and the sodium acetate buffer constitutes about 6–8 percent.

In another embodiment of the invention, the alcohol is methanol, and the anti-clumping agent is preferably a combination of sodium and potassium EDTA salts, and the buffering agent is an acetate buffer. In one embodiment, the solution comprises methanol, magnesium acetate, calcium acetate, potassium chloride, and sodium chloride. The alcohol constitutes approximately 20 percent of the solution, about 0.1% sodium chloride, 10 mM potassium chloride, 2 mM calcium acetate, and 1 mM magnesium acetate.

In an illustrative practice of the method of the invention, a sample of mammalian cells is provided and, within a predetermined or specified time frame following biopsy, the cells are suspended in a preservation solution of the type described above. In one embodiment of the invention, the suspended cells can be preserved at an ambient temperature in the range of from about 4° to about 38° centigrade (C.) for a period of at least approximately three weeks. Throughout this time, the cells retain sufficient structure to enable staining without a significant loss of integrity.

In another illustrative practice of the method of the invention, a sample of mammalian cells is provided and, within a specified time frame following biopsy, the cells are suspended in a preservation solution of the invention. In that embodiment of the invention, the sample is placed in the preservation solution to remove undesired protein from the cell sample. The clean sample may then be transported in the inventive solution for subsequent analysis and/or storage.

DETAILED DESCRIPTION OF THE INVENTION

The present invention generally relates to an alcohol-buffer solution for the preservation of mammalian cells in suspension at ambient temperature. The solution enhances maintenance of the nuclear structure of the cells, in that it maintains cell membranes intact for subsequent cytological staining. The solution also effectively destroys microbial pathogens in a sample, and inhibits retroviral activity. In one form, the solution removes undesired protein material from the sample.

More particularly, the cell-preservation solution of the invention includes a combination of an alcohol, an anti-clumping agent, and a buffer that maintains the solution at a pH of between about four to seven for the duration of the preservation time.

In one embodiment, the preservation time for cells in the present solutions at ambient temperature (approximately 37° C.), is approximately three weeks. This duration may be altered by both the stored age of the solution prior to ambient cell suspension, the amount of time between cell sampling and cell suspension, and the alcohol content. For example, if the solution has been stored for a significant length of time, in either a refrigerated state or an ambient state, then the remaining cell-preserving viability of the solution may be limited.

In a preferred embodiment, the alcohol is methanol. Other alcohols which may be used include isopropanol and ethanol among others. This alcohol consituent maintains cell DNA integrity and retains the detail of the cell nucleus for subsequent cytological staining and analysis.

In one embodiment of the invention, the alcohol is present in an amount of approximately 45% to 55% by solution. Solutions containing 60% or above of the alcohol constituent tend to exhibit clumping, or coagulation, which interferes with the subsequent ability to affectively stain the sample cells. Conversely, if the concentration of alcohol in this embodiment is at 40% or below, the cells are not sufficiently fixed for relatively long-term preservation, causing the cells to degrade over time. For this embodiment, the solution contains approximately 50% methanol, by solution.

In another embodiment of the invention, the alcohol is present in an amount approximately 20 percent by solution. While this concentration of alcohol, as noted above, does not enable long-term preservation, (i.e., over two days), it does sufficiently fix cells for subsequent analysis. Alternatively, the cells may be transferred from this 20% embodiment solution to a 50% embodiment of the solution, for subsequent long-term preservation prior to analysis.

The inventive solution also contains an anti-clumping agent in an amount sufficient to prevent cell clumping. In one embodiment, the anti-clumping agent is the chelating agent ethylene diamine tetraacetate (EDTA), with the preferred form being the disodium salt. Other chelating agents deemed useful as the anti-clumping agent include cuminin, heparin, streptokinase, and such agents found in lysing or anticoagulant compositions.

The buffer used in the inventive solution has a large buffering range to accommodate for the change in pH resulting from autolytic by-products from the sample cells suspended in the solution. For example, as cervical cells age, they release autolytic by-products that alter the pH balance of the suspension solution. In addition, the preservation of different cell types may require solutions of different acidity and within different pH ranges. Accordingly, a solution having a broad buffering range can be used for a wide range of cell types and is optimal for the solution of the invention. Exemplary cells for which this solution can be used include cervical cells, white blood cells, bronchial cells, and sputum, among others.

Accordingly, a preferred buffer is an acetate buffer, such as sodium acetate, magnesium acetate, calcium acetate, and combinations thereof. While other buffers, such as phosphate or Tris buffers, may be used in the present solution, the effective buffering range of these buffers is deemed to be not as broad at the desired PH as that of acetate.

In addition to being a cell preservative, the inventive solution also kills selected pathogens. For example, in test samples the solution effectively kills the following organisms: *Candida albicans, Aspergillus niger, Escherichia coli, Pseudomonas aeruginosa,* and *Staphylococcus aureus.* This activity is shown in further detail in Example 1 below.

In practicing the method of the invention, a cell sample is obtained from a patient or other cell source. A preservation solution of the type described above is placed either in a vial, on a welled slide, or on an appropriate membrane. The collected cells are then placed in the solution, preferably within one minute following collection. The sooner the collected cells are placed in the preservative solution, the longer the cells can be preserved at ambient temperature suspended in the solution, since the trauma to the cells is minimized.

Following preservation and/or protein removal, when the cells are to be stained or otherwise analyzed, a device can be used to remove suspended cells, along with the suspension preservation medium, and place them on a slide or other appropriate surface for further processing.

The invention is described further in the following non-limiting examples.

EXEMPLIFICATION

EXAMPLE 1

Approximately 20 ml of the preservation solution described above, having the following composition, were aseptically placed in sterile centrifuge tubes, along with an aliquot of one organism to be tested. All samples were plated on Letheen agar. The composition of the preservation solution was:

249 g 180 mM sodium acetate
6 ml 100 mM glacial acetic acid
500 ml methanol
500 ml deionized $H_2O$ The pH of the resulting solution was adjusted to approximately 5.8. The following organisms were tested for viability, each obtained from the ATCC:

| Organism | ATCC No. |
|---|---|
| *Candida albicans* | 10231 |
| *Aspergillus niger* | 16404 |
| *Escherichia coli* | 8739 |
| *Pseudomonas aeruginosa* | 9027 |
| *Staphylococcus aureus* | 6538 |

The following test results were obtained:

| Organism | Initial Stock Concentration | organisms/ml Time 0 | 30 Mins. | 3 Hrs. |
|---|---|---|---|---|
| C. albicans | $2.9 \times 10^7$ | <1000 | <10 | <10 |
| A. niger | $5.6 \times 10^7$ | $3.6 \times 10^5$ | <10 | <10 |
| E. coli | $2.35 \times 10^7$ | $2.3 \times 10^5$ | <10 | <10 |
| P. aeruginosa | $2.0 \times 10^7$ | <1000 | <10 | <10 |
| S. aureus | $3.0 \times 10^7$ | $1.5 \times 10^5$ | <10 | <10 |

These results show that the preservative solution of the present invention effectively kills organisms, such as those listed above. In many prior preservative solutions, these organisms frequently multiply in samples, obscuring or interfering with the study of the desired cells. Thus, the solution having the above-identified composition can be used as an antimicrobial solution, in addition to being used as a cell preservative.

EXAMPLE 2

One composition of the preservative solution of the present invention consists of 50% methanol in acetate buffer. The specific formula used in this example, Solution A, is as follows:

3.2 ml glacial acetic acid ($CH_3COOH$)
7.2 ml 5N NaOH
89.6 ml distilled $H_2O$
100 ml methanol (MeOH)

A solution of phosophate buffered saline (PBS) in 20% ethanol was used as a control solution, Solution B. A third solution, Solution C, consisted of phosphate buffer, without the saline (NaCl), mixed with the 50% methanol Solution B. The pH of the phosphate buffer solution was initially 7.85. Following the addition of 50 methanol, the pH increased to 9.02. Sodium phosphate monobasic monohydrate ($NaH_2PO_4$) was added (2.8 g), resulting in a lowered PH of 6.52. The solution was reused to pH 7.5 with 50 methanol.

Cervical cell samples were taken and stored overnight in PBC at 40° C. Samples were pooled, and two 13 ml samples were pipetted into 50 ml centrifuge tubes Samples A and B, respectively), and one 15 ml sample was pipetted into a 50 ml centrifuge tube (Sample C). All three samples were centrifuged for 10 minutes at maximum setting, and the supernatant discarded. Aliquots of Solutions A and B (40 ml each) were added to the remaining pellets of Samples A and B, respectively, while a 50 ml aliquot of Solution C was added to the pellet of Sample C. The following procedure was performed on day zero, then once a week for three weeks, for each sample.

The samples were lightly vortexed to disperse the pellets. Aliquots of 10 ml each were taken from each Sample tube, and placed in a rotor cylinder. The sampes were rotored for 15 seconds at 8V (482 rpm/V). Two slides, having 5 ml of specimen per slide) were prepared and fixed in 95% ethanol for 30 minutes. One of the two slides was immediately stained using routine Pap stain. The second slide was allowed to dry, post-fixation, in a covered dish to be batch stained at the end of the study to reduce stain viability bias.

The following qualitative results were observed:

| Soln A | Week | Morphology |
|---|---|---|
| 4° | 0 | slight air drying, esp. in inflammatory cells |
|  | 1 | superior to day 0, esp. inflammatory and epithelial cells |
|  | 2 | same as week 1 |
|  | 3 | same as week 1; background debris noted |
| room temp. | 0 | air drying observed |
|  | 1 | abnormal cells noted; retains diagnostic features |
|  | 2 | endocervical cells preserved; same as week 1 |
|  | 3 | same as week 1 |
| 37° | 0 | same as for 4° and room temp specimens, i.e., air drying |
|  | 1 | rare degeneration in abnormals |
|  | 2 | abnormal architecture; morphology intact; slight degeneration |
|  | 3 | same as week 2; endocervical cells noted; background debris noted |

| Soln B | Week | Morphology |
|---|---|---|
| 4° | 0 | some air drying |
|  | 1 | degeneration noted in inflammatory cells (fuzzy) |
|  | 2 | good preservation; endocervical cells maintained |
|  | 3 | inflammatory cells less crisp |
| room temp | 0 | air drying |
|  | 1 | rolling noted |
|  | 2 | good endocervical cell preservation; increased HK (large gaps); abnormal cells; decrease in cytological detail |
|  | 3 | endocervical cells preserved; increased epithelial nuclear degeneration |
| 37° | 0 | air drying |
|  | 1 | rolling; degeneration in inflammatory cells |
|  | 2 | degenerated inflammatory cells |
|  | 3 | degenerated inflammatory cells; some degenerative changes in abnormal cells; rare number of abnormal cells |

| Soln C | Week | Morphology |
|---|---|---|
| 4° | 0 | marked degeneration in inflammatory cells |
|  | 1 | no inflammatory cell preservation; rare abnormal cells; poor nuclear/cytoplasmic preservation of either normal and abnormal cells |
|  | 2 | same as for week 1 |
|  | 3 | marked degeneration |

These test results demonstrate that optimal results are from Solution A. In that solution, cells remain well-preserved up to three weeks. Some degeneration seen in abnormal cells may be biological in nature.

EXAMPLE 3

The above experiment (Example 2) was performed on cervical specimens known to contain abnormal cells. Such cells included rare squamous atypia (ASM), mild dysplasia (LG), koilacytotic atypia (HPV), and endocervical cells (EC). The results were as follows:

| Soln A | Week | Morphology |
|---|---|---|
| 4° | 0 | LG; HPV; ASM; reacting EC's |
|  | 1 | LG; HPV; sheets of EC's |
|  | 2 | LG; HPV; EC's noted |
|  | 3 | LG; HPV; sheets of EC's; slight nuclear/cytoplasmic degeneration |
| room temp | 0 |  |
|  | 1 | LG; rare HPV, rare koilo, reactin EC's |
|  | 2 | LG; HPV; reacting EC's |
|  | 3 | LG; HPV; (metaplastic features); sheets of EC's; Candida noted |
| 37° | 0 |  |
|  | 1 | LG; HPV (metaplastic features); sheets of EC's; nuclear wrinkling |
|  | 2 | rare LG; rare HPV; EC's noted |

| Soln A | Week | Morphology |
|--------|------|------------|
|        | 3    | LG; HPV; EC's noted |

Superior morphology was maintained throughout the study. Abnormal cytologic detail was maintained at all temperatures over the three week period. These results demonstrate that Solution A is optimal for collection and transportation of cell samples.

EXAMPLE 4

A general formula for an alternate embodiment of the preservation solution of the invention is stated as follows:

| N/2 liters | deionized $H_2O$ |
| N × 1.116 g | $Na_2$ EDTA.$2H_2O$ |
| N × 0.35 ml | glacial acetic acid |
| (45–55%) | methanol | wherein N represents the final batch solution size. Methanol is added in an amount up to N, within the desired percentage range.

EXAMPLE 5

Another embodiment of the invention includes the following formulation:
1 mM magnesium acetate
2 mM calcium acetate
10 mM potassium chloride
0.1% sodium chloride
20% methanol In this formulation, the function of the calcium and magnesium ions is the preservation of nuclear morphology of cytologically significant cells. The acetate is present as a buffer that will both stabilize the pH of the solution, and not form precipitates of calcium and magnesium. Such precipitation would happen with a phosphate buffer. The sodium and potassium salts are present to help stabilize the cells and prevent precipitation and coagulation of hemoglobin and other serum proteins. The methanol is present to aid in the lysing of red blood cells, to act as a preservative against bacterial growth, and to help preserve cytologically significant cells.

The invention can be embodied in other specific forms without departing from the spirit or essential characteristics thereof. The present embodiments are therefore to be considered in all respects as illustrative and not restrictive. The scope of the invention is indicated by the appended claims, rather than by the foregoing description, and all changes which come within the meaning and range of equivalency of the claims are therefore intended to be embraced therein.

What is claimed as new and secured by Letters Patent is:

1. An aqueous alcohol-buffer solution for maintaining the structural integrity of mammalian cells in vitro, said solution comprising
   A. a water-miscible alcohol in an amount sufficient to fix mammalian cells,
   B. an anti-clumping agent in an amount sufficient to prevent the mammalian cells from clumping in said solution, and
   C. a buffering agent which maintains said solution, with the mammalian cells, at a pH range of between about two to about seven.

2. The solution of claim 1 wherein said alcohol is selected from the group consisting of ethanol, isopropanol, and methanol.

3. The solution of claim 1 wherein said alcohol is methanol.

4. The solution of claim 1 wherein said anti-clumping agent is a chelating agent selected from the group consisting of ethylenediamine tetraacetic acid and salts thereof.

5. The solution of claim 1 wherein said anti-clumping agent is ethylenediamine tetraacetic acid.

6. The solution of claim 1 wherein said alcohol constitutes about 45 to about 55 percent of said solution.

7. The solution of claim 1 wherein said alcohol constitutes about 50 percent of said solution.

8. The solution of claim 1 wherein said buffering agent is selected from the group consisting of phosphate buffered saline, Tris buffer, sodium acetate, ethylenediamine tetraacetic acid, ethylenediamine tetraacetic acid salts, citric aid and citric acid salts.

9. The solution of claim 1 wherein said buffering agent is sodium acetate.

10. An aqueous alcohol-buffer solution for maintaining the structural integrity of mammalian cells in vitro, said solution comprising, by volume,
    A. about forty-five to fifty-five percent methanol,
    B. about two to four percent acetic acid, and
    C. about six to eight percent sodium acetate buffer.

11. The solution of claim 10 comprising about 50 percent methanol.

12. The solution of claim 10 comprising about three percent acetic acid.

13. The solution of claim 10 comprising about seven percent sodium acetate buffer.

14. The solution of claim 1 wherein said alcohol constitutes about 20 percent of said solution.

15. The solution of claim 1 wherein said anti-clumping agent is an ethylenediamine tetraacetic acid salt selected from the group consisting of sodium and potassium.

* * * * *